United States Patent
Mahmood et al.

(10) Patent No.: US 12,376,061 B2
(45) Date of Patent: Jul. 29, 2025

(54) WEARABLE DEVICE AND METHOD

(71) Applicant: Prevayl Innovations Limited, Manchester (GB)

(72) Inventors: Tahir Mahmood, Manchester (GB); Samuel Bird, Manchester (GB)

(73) Assignee: Prevayl Innovations Limited, Wilmslow (GB)

( * ) Notice: Subject to any disclaimer, the term of this patent is extended or adjusted under 35 U.S.C. 154(b) by 550 days.

(21) Appl. No.: 17/627,218

(22) PCT Filed: Aug. 6, 2020

(86) PCT No.: PCT/GB2020/051885
§ 371 (c)(1),
(2) Date: Jan. 14, 2022

(87) PCT Pub. No.: WO2021/028661
PCT Pub. Date: Feb. 18, 2021

(65) Prior Publication Data
US 2022/0264510 A1     Aug. 18, 2022

(30) Foreign Application Priority Data

Aug. 9, 2019 (GB) ..................................... 1911412

(51) Int. Cl.
*H04W 60/04*     (2009.01)
*A61B 5/00*      (2006.01)
(Continued)

(52) U.S. Cl.
CPC ........... *H04W 60/04* (2013.01); *A61B 5/6804* (2013.01); *H04B 1/385* (2013.01); *H04W 52/0254* (2013.01)

(58) Field of Classification Search
CPC ..... H04W 88/06; H04W 84/12; H04W 48/18; H04W 4/80; H04W 76/15; H04W 8/183; H04W 76/14; H04W 48/16; H04W 24/02
See application file for complete search history.

(56) References Cited

U.S. PATENT DOCUMENTS 7,769,412 B1 *  8/2010  Gailloux ................. H04M 1/05
                                                    455/420
9,442,523 B2 *  9/2016  Lee ........................ G06F 1/3231
(Continued)

FOREIGN PATENT DOCUMENTS

CN     201394012      2/2010
EP     3 431 002      1/2019
(Continued)

OTHER PUBLICATIONS

GB Combined Search Report and Examination Report dated Jan. 29, 2021 of GB Application 1911427.1.
(Continued)

*Primary Examiner* — Diana J. Cheng
(74) *Attorney, Agent, or Firm* — Haley Guiliano LLP

(57) ABSTRACT

The wearable device (10) comprises a liveness detection module (103) arranged to detect whether the wearable device (10) is being worn by a user. The wearable device (10) comprises an activation message module (105) arranged to generate an activation message for requesting that wireless network services be activated for the wearable device (10) in response to the liveness detection module detecting that the wearable device is being worn. The wearable device (10) comprises a communicator (107) arranged to transmit the activation message to a server operable to activate wireless network services for the wearable device (10). The wireless network services are to be activated for a first wireless network. The communicator
(Continued)

(107) is arranged to transmit the activation message via a second wireless network that the wearable device (10) is activated to transmit data on.

20 Claims, 4 Drawing Sheets

(51) Int. Cl.
*H04B 1/3827* (2015.01)
*H04W 52/02* (2009.01)

(56) References Cited

U.S. PATENT DOCUMENTS

| | | |
|---|---|---|
| 10,216,312 B2 * | 2/2019 | Park .................. H04N 23/45 |
| 10,659,949 B2 * | 5/2020 | Kim .................. H04W 4/023 |
| 11,589,212 B2 * | 2/2023 | Lee .................. H04W 12/40 |
| 2012/0041278 A1 | 2/2012 | Sadhu |
| 2013/0072765 A1 | 3/2013 | Kahn et al. |
| 2014/0024361 A1 | 1/2014 | Poon et al. |
| 2015/0145671 A1 | 5/2015 | Cohen et al. |
| 2016/0026212 A1 | 1/2016 | Lee et al. |
| 2016/0241553 A1 | 8/2016 | Kim |
| 2016/0337843 A1 | 11/2016 | Repka et al. |
| 2017/0048652 A1 | 2/2017 | Del Rio et al. |
| 2018/0014787 A1 | 1/2018 | Ganton et al. |
| 2018/0115935 A1 | 4/2018 | Targali et al. |
| 2019/0104401 A1 | 4/2019 | Park et al. |
| 2019/0125259 A1 | 5/2019 | Huang |
| 2019/0138068 A1 | 5/2019 | Park et al. |
| 2019/0174296 A1 | 6/2019 | Kim et al. |

FOREIGN PATENT DOCUMENTS

| | | |
|---|---|---|
| KR | 101760233 | 7/2017 |
| KR | 20180050127 | 5/2018 |
| WO | WO 2006079953 | 8/2006 |
| WO | WO 2008072168 | 6/2008 |
| WO | WO 2010120945 | 10/2010 |
| WO | WO 2016051268 | 4/2016 |
| WO | WO 2017004158 | 1/2017 |
| WO | WO 2018083246 | 5/2018 |

OTHER PUBLICATIONS

GB Combined Search Report and Examination Report dated Jan. 27, 2020 of GB Application 1911412.3.
GB Combined Search Report and Examination Report dated Sep. 8, 2021 of GB Application 2111947.4.
International Search Report and Written Opinion of PCT/GB2020/051889 dated Dec. 8, 2020.
International Search Report and Written Opinion of PCT/GB2020/051885 dated Sep. 14, 2020.
U.S. Appl. No. 17/627,272, filed Jan. 14, 2022, Tahir MahMood

* cited by examiner

WEARABLE DEVICE AND METHOD

CROSS-REFERENCE TO RELATED APPLICATIONS

This application is a national stage application under 35 U.S.C. § 371 of International Application PCT/GB2020/051885, filed Aug. 6, 2020, which claims priority of GB Patent Application 1911412.3, filed Aug. 9, 2019. The disclosure of which are hereby incorporated by reference herein in their entireties.

BACKGROUND

The present invention is directed towards a wearable device and method, and in particular a wearable device and method for use in activating wireless network services for the garment. The wearable device may be a garment.

Garments incorporating sensors are wearable electronics which can be designed to interface with a wearer of the garment, and to determine information such as the wearer's heart rate, rate of respiration, activity level, and body positioning. Such properties can be measured with a sensor assembly that includes a sensor for signal transduction and/or microprocessors for analysis. Such garments are commonly referred to as 'smart clothing' and may be referred to as 'biosensing garments' if they measure biosignals. Typically such garments are only able to communicate locally with a user phone via a short range communication protocol such as NFC or Bluetooth. Typically, such garments are directly paired to a particular phone.

It is desirable to enable garments to communicate over long range communication protocols such as cellular networks. It is particularly desirable to provide an improved process for activating garments to communicate over a wireless network.

SUMMARY

According to the present disclosure there is provided a wearable device and method as set forth in the appended claims. Other features of the invention will be apparent from the dependent claims, and the description which follows.

According to a first aspect of the present disclosure, there is provided a garment. The garment comprises a liveness detection module arranged to detect whether the garment is being worn by a user. The garment comprises an activation message module arranged to generate an activation message for requesting that wireless network services be activated for the garment in response to the liveness detection module detecting that the garment is being worn. The garment further comprises a communicator arranged to transmit the activation message to a server operable to activate wireless network services for the garment.

Beneficially, the garment transmits (e.g. automatically, without user input) an activation message for requesting that wireless network services be activated for the garment in response to detecting that the garment is being worn by the user. In this way, the simple act of wearing the garment can be used to activate wireless network services. This may help reduce battery consumption as the device may only be activated to transmit data when worn.

The activation message may be transmitted directly by the garment to the server over, for example, the wireless network, and in particular over a provisioning channel of the wireless network. The activation message may be transmitted indirectly to the server, e.g. via one or more other electronic devices arranged to communicate over the wireless network. The activation message may be transmitted over a secure communication channel and/or may be encrypted. The communicator may be arranged to receive an activation message response from the server that the activation message is transmitted to. The garment may perform additional actions such as transmit garment data (e.g. biosensing data) on the wireless network in response to receiving the activation message response.

If the liveness detection module detects that the garment is not being worn by the user, the liveness detection module may be arranged to control the garment to power-off or transition to a reduced power mode. The reduced power mode may be a standby or hibernation mode.

Prior to the liveness detection module detecting that the garment is being worn by a user, the garment may be arranged to operate in a low power mode. Advantageously, this reduces power consumption for the garment as the garment will operate in a low power mode until the liveness detection module detects that the garment is being worn. The device may only transmit data when worn. Reducing power consumption is important for garments and other wearable devices as typically small battery modules are desired so as not to increase the weight or bulk of the garment.

If the liveness detection module detects that the garment is being worn by a user, the garment may be arranged to transition from the low power mode to a normal mode. The normal power mode is a mode of increased power consumption relative to the low power mode. In the low power mode the communicator may not be activated to transmit data. In the normal mode, the communicator may be activated to transmit data. In the low power mode, the liveness detection module will be active to detect whether the garment is being worn but other components of the garment may be deactivated or otherwise operating in a low power state.

The wireless network services to be activated may be over a first wireless network. The communicator may be arranged to transmit the activation message via a second wireless network that the garment is activated to transmit data on. The first and second wireless networks may be different from one another. The first wireless network may be a cellular network. The second wireless network may be a local wireless network. Advantageously, this approach enables a garment which may lack the credentials to access the first wireless network to activate wireless network services for the first wireless network by communicating over a second wireless network. The communication over the second wireless network may be facilitated by a user equipment that receives the activation message from the garment over the first wireless network and communicates with the server to activate the wireless network services for the garment over the first wireless network.

The activation message may further comprise identification information for the garment. The identification information for the garment may comprise identification information for an electronics module that is removably coupled to the garment. The identification information for the garment may comprise a unique identifier for the garment and/or a subscriber identifier for the garment which uniquely identifies the garment on the mobile network. The subscriber identifier may comprise a mobile subscription identification number (MSIN). The subscriber identifier may comprise an international mobile subscriber identity (IMSI).

The garment may comprise a Universal Integrated Circuit Card (UICC) that enables the garment to access services provided by a mobile network operator (MNO). MNOs include virtual mobile network operators (VMNOs). The UICC may include at least a read-only memory (ROM) configured to store an MNO profile that the garment can utilize to register and interact with an MNO. The UICC may be in the form of a Subscriber Identity Module (SIM) card. The garment may have a receiving section arranged to receive the SIM card. In other examples, the UICC is embedded directly into a controller of the garment. That is, the UICC may be an electronic/embedded UICC (eUICC). A eUICC is beneficial as it removes the need to store a number of MNO profiles, i.e. electronic Subscriber Identity Modules (eSIMs). Moreover, eSIMs can be remotely provisioned to garments. The garment may comprise a secure element that represents an embedded Universal Integrated Circuit Card (eUICC).

eSIMs may be pre-generated with a basic set of information, and may be later assigned to garments when requests are received. A manufacturer may assign each garment with a first unique identifier. The manufacturer may receive a plurality of subscriber identifiers from a mobile network operator. The manufacturer may link each first unique identifier to a different one of the subscriber identifiers. That is, eSIMs may be pre-generated and provided to the garment manufacturer who may then choose how to assign the eSIMs to the garments.

The garment may comprise one or more sensors. The garment may sense one or more signals external to the wearer. The garment may comprise any or a combination of a temperature sensor, a camera, a location tracking module such as a GPS module, and a chemical sensor.

The garment may sense a combination of external signals and biosignals of the wearer. The garment may be a biosensing garment. The biosensing garment may comprise a biosensing unit for measuring biodata/biosignals of the wearer. Here, "biosignal" may refer to any signal in a living being that can be measured and monitored. The term "biosignal" is not limited to electrical signals and can refer to other forms of non-electrical biosignals. A biosensing unit therefore refers to an electronic component that is able to measure a biosignal of the wearer. The biosensing unit may comprise one or more electrodes but is not limited to this arrangement. The biosensing unit may be a textile-based biosensing unit. The terms "biosignal" and "biodata" are used synonymously throughout the specification.

The garment may comprise one or more biosensing units. The biosensing unit may be used for measuring one or a combination of bioelectrical, bioimpedance, biochemical, biomechanical, bioacoustics, biooptical or biothermal signals of the wearer. The bioelectrical measurements include electrocardiograms (ECG), electrogastrograms (EGG), electroencephalograms (EEG), and electromyography (EMG). The bioimpedance measurements include plethysmography (e.g., for respiration), body composition (e.g., hydration, fat, etc.), and electroimpedance tomography (EIT). The biomagnetic measurements include magnetoneurograms (MNG), magnetoencephalography (MEG), magnetogastrogram (MGG), magnetocardiogram (MCG). The biochemical measurements include glucose/lactose measurements which may be performed using chemical analysis of the wearer's sweat. The biomechanical measurements include blood pressure. The bioacoustics measurements include phonocardiograms (PCG). The biooptical measurements include orthopantomogram (OPG). The biothermal measurements include skin temperature and core body temperature measurements. The biosensing unit may comprise a radar unit.

The garment may comprise a controller in communication with a sensor of the garment such as the biosensing unit and operable to control the sensor or the biosensing unit. The controller may be wirelessly connected to the sensor or the biosensing unit. That is, the sensor/biosensing unit may comprise a communicator for wireless communication with the controller. The controller may be conductively connected to the sensor/biosensing unit. The controller may be conductively connected to the sensor/biosensing unit by a conductor. The conductor may be incorporated into the garment. The conductor may be an electrically conductive track or film. The conductor may be a conductive transfer. The conductive transfer may comprise a first non-conductive ink layer and a second non-conductive ink layer. An electrically conductive layer may be positioned between the first non-conductive ink layer and the second non-conductive ink layer. The conductive transfer may be adhered to the textile via use of an adhesive layer so as to form the conductor on the textile. The conductor may be formed from a fibre or yarn of the textile. This may mean that an electrically conductive materials are incorporated into the fibre/yarn.

The garment may further comprise a power source or a plurality of power sources. The power source may be for powering the sensor/biosensing unit. The power source may be conductively connected to the controller by a conductor. The conductor may be a conductive transfer. The conductor may be formed from a fibre or yarn of the garment. This may mean that an electrically conductive materials such as graphene is incorporated into the fibre/yarn. The power source may be a battery. The battery may be a rechargeable battery. The battery may be a rechargeable battery adapted to be charged wirelessly such as by inductive charging. The power source may comprise an energy harvesting device. The energy harvesting device may be configured to generate electric power signals in response to kinetic events such as kinetic events performed by a wearer of the garment. The kinetic event could include walking, running, exercising or respiration of the wearer. The energy harvesting material may comprise a piezoelectric material which generates electricity in response to mechanical deformation of the converter. The energy harvesting device may harvest energy from body heat of a wearer of a garment. The energy harvesting device may be a thermoelectric energy harvesting device.

The communicator may be a mobile/cellular communicator operable to communicate the data wirelessly via one or more base stations. The communicator may provide wireless communication capabilities for the garment and enables the garment to communicate via one or more wireless communication protocols such as used for communication on: a wireless wide area network (WWAN), a wireless metroarea network (WMAN), a wireless local area network (WLAN), a wireless personal area network (WPAN), a near field communication (NFC), and a cellular communication network. The cellular communication network may be a fourth generation (4G) LTE, LTE Advanced (LTE-A), fifth generation (5G), sixth generation (6G), and/or any other present or future developed cellular wireless network. A first communicator on the garment may be provided for cellular communication and a separate communicator may be provided for short-range local communication over WLAN, WPAN, NFC, or Bluetooth®, WiFi or any other electromagnetic RF communication protocol.

The garment may refer to an item of clothing or apparel. The garment may be a top. The top may be a shirt, t-shirt, blouse, sweater, jacket/coat, or vest. The garment may be a dress, brassiere, shorts, pants, arm or leg sleeve, vest, jacket/coat, glove, armband, underwear, headband, hat/cap, collar, wristband, stocking, sock, or shoe, athletic clothing, swimwear, wetsuit or drysuit The garment may be constructed from a woven or a non-woven material. The garment may be constructed from natural fibres, synthetic fibres, or a natural fibre blended with one or more other materials which can be natural or synthetic. The yarn may be cotton. The cotton may be blended with polyester and/or viscose and/or polyamide according to the particular application. Silk may also be used as the natural fibre. Cellulose, wool, hemp and jute are also natural fibres that may be used in the garment. Polyester, polycotton, nylon and viscose are synthetic fibres that may be used in the garment.

According to a second aspect of the present disclosure there is provided a server operable to activate wireless network services for a garment. The server comprises a communicator operable to receive an activation message from a garment, the activation message requesting that wireless network services be activated for the garment. The server comprises a determination module operable to determine whether to activate wireless network services for the garment. The server comprises an activation module operable to activate wireless network services for the garment as a result of the determination. That is, the activation module is operable to activate wireless network services in response to the determination module determining to activate wireless network services.

The activation message may comprise identification information for the garment. The determination module may be arranged to use the identification information to determine whether to activate wireless network services for the garment. The determination module may be arranged to compare the identification information to a database which stores identification information for different garments along with status information for the garments. The status information may include whether the garment has a data plan on the wireless network. If the determination module determines, from the status information, that the garment is authorised to be activated, then the activation module may activate wireless network services for the garment. If the server determines, from the status information, that the garment is not authorised to be activated (e.g. is not associated with a data plan) then the server may not activate wireless network services for the garment.

The identification information for the garment may comprise a unique identifier for the garment and/or a subscriber identifier for the garment which uniquely identifies the garment on the mobile network. The subscriber identifier may comprise a mobile subscription identification number (MSIN). The subscriber identifier may comprise an international mobile subscriber identity (IMSI). The server may use the subscriber identifier that uniquely identifies the garment on the wireless network to activate wireless network services. The server may use the subscriber identifier to identity the status information for the garment. The server may be a mobile network operator, MNO, server. The server may interact with a mobile network operator, MNO, server e.g. via using an Application Programming Interface (API). The server may be a virtual mobile network operator server. The server may be a Home Location Register or Visitor Location Register.

The activation message may be received on a provisioning channel of the wireless network.

The wireless network services may be arranged to be activated for a first wireless network. The activation message may be received via a second wireless network that the garment is activated to transmit data on.

The identification information may comprise, encoded therein, the subscriber identifier. Using the identification information to obtain the subscriber identifier may comprise decoding the identification information to obtain the subscriber identifier. That is, the identification information may be an encoded/encrypted representation of the subscriber identifier. This makes it harder for a hostile party monitoring the communication to obtain the subscriber identifier.

The identification information for the garment may be a first unique identifier for the garment. The subscriber identifier may be a second unique identifier for the garment. Beneficially, the subscriber identifier is not transmitted over a communication channel and thus is not accessible by a hostile party. Instead, a first unique identifier is transmitted which is subsequently used to obtain the subscriber identifier. The first unique identifier may only identify the garment and may not have any information content that relates to the subscriber identifier.

The server may receive encoded data representing the first unique identifier. The server may be arranged to decode the encoded data to obtain the first unique identifier.

The server may be arranged to use the first unique identifier to obtain the second unique identifier for the garment. The server may be arranged to access a data store that associates each of a plurality of different first unique identifiers with a different one of a plurality second unique identifiers; and may be arranged to obtain the second unique identifier that is associated with the received first unique identifier in the data store. That is, the server may store or have access to a data store which links each garment identifier (first unique identifier) to a different subscriber identifier (second unique identifier).

According to a third aspect of the present disclosure, there is provided a method of requesting wireless network services by for a garment. The method comprises detecting, by the garment, whether the garment is being worn by a user. In response to detecting that the garment is being worn, the method comprises generating, by the garment, an activation message for requesting that wireless network services be activated for the garment. The method further comprises transmitting, by the garment, the activation message to a server operable to activate wireless network services for the garment.

According to a fourth aspect of the present disclosure, there is provided a method of activating wireless network services for a garment. The method comprises receiving, by the server, an activation message from a garment, the activation message requesting that wireless network services be activated for the garment. The method comprises determining, by the server, whether to activate wireless services for the garment. The method comprises activating wireless network services as a result of the determination. That is, the wireless network services are activated in response to determining to activate wireless network services.

According to a fifth aspect of the present disclosure, there is provided a computer readable medium having instructions recorded thereon which, when executed by a computer, cause the computer to perform the method as described above in relation to the third or fourth aspect of the present disclosure.

According to a sixth aspect of the present disclosure, there is provided a computer program comprising instructions which, when executed by a computer, cause the computer to carry out the method as described above in relation to the third or fourth aspect of the present disclosure.

According to a sixth aspect of the present disclosure, there is provided a system. The system comprises a garment and a server. The garment comprises a liveness detection module arranged to detect whether the garment is being worn by a user. The garment comprises an activation message module arranged to, generate an activation message for requesting that wireless network services be activated for the garment in response to the liveness detection module detecting that the garment is being worn. The garment further comprises a communicator arranged to transmit the activation message to the server operable to activate wireless network services for the garment. The server comprises a communicator operable to receive the activation message from the garment. The server comprises a determination module operable to determine whether to activate wireless network services for the garment. The server comprises an activation module operable to activate wireless network services for the garment as a result of the determination.

The present disclosure is not limited to garments. The aspects of the present disclosure can be applied to any device for which it is desirable to activate wireless network services. The device may be a mobile phone, tablet computer, gaming system, MP3 player, point-of-sale device, or wearable device such as a smart watch, necklace, bracelet, or glasses.

BRIEF DESCRIPTION OF THE DRAWINGS

Examples of the present disclosure will now be described with reference to the accompanying drawings, in which.

DETAILED DESCRIPTION

The following description with reference to the accompanying drawings is provided to assist in a comprehensive understanding of various embodiments of the disclosure as defined by the claims and their equivalents. It includes various specific details to assist in that understanding but these are to be regarded as merely exemplary. Accordingly, those of ordinary skill in the art will recognize that various changes and modifications of the various embodiments described herein can be made without departing from the scope and spirit of the disclosure. In addition, descriptions of well-known functions and constructions may be omitted for clarity and conciseness.

The terms and words used in the following description and claims are not limited to the bibliographical meanings, but, are merely used by the inventor to enable a clear and consistent understanding of the disclosure. Accordingly, it should be apparent to those skilled in the art that the following description of various embodiments of the disclosure is provided for illustration purpose only and not for the purpose of limiting the disclosure as defined by the appended claims and their equivalents.

It is to be understood that the singular forms "a," "an," and "the" include plural referents unless the context clearly dictates otherwise.

Figure 1:
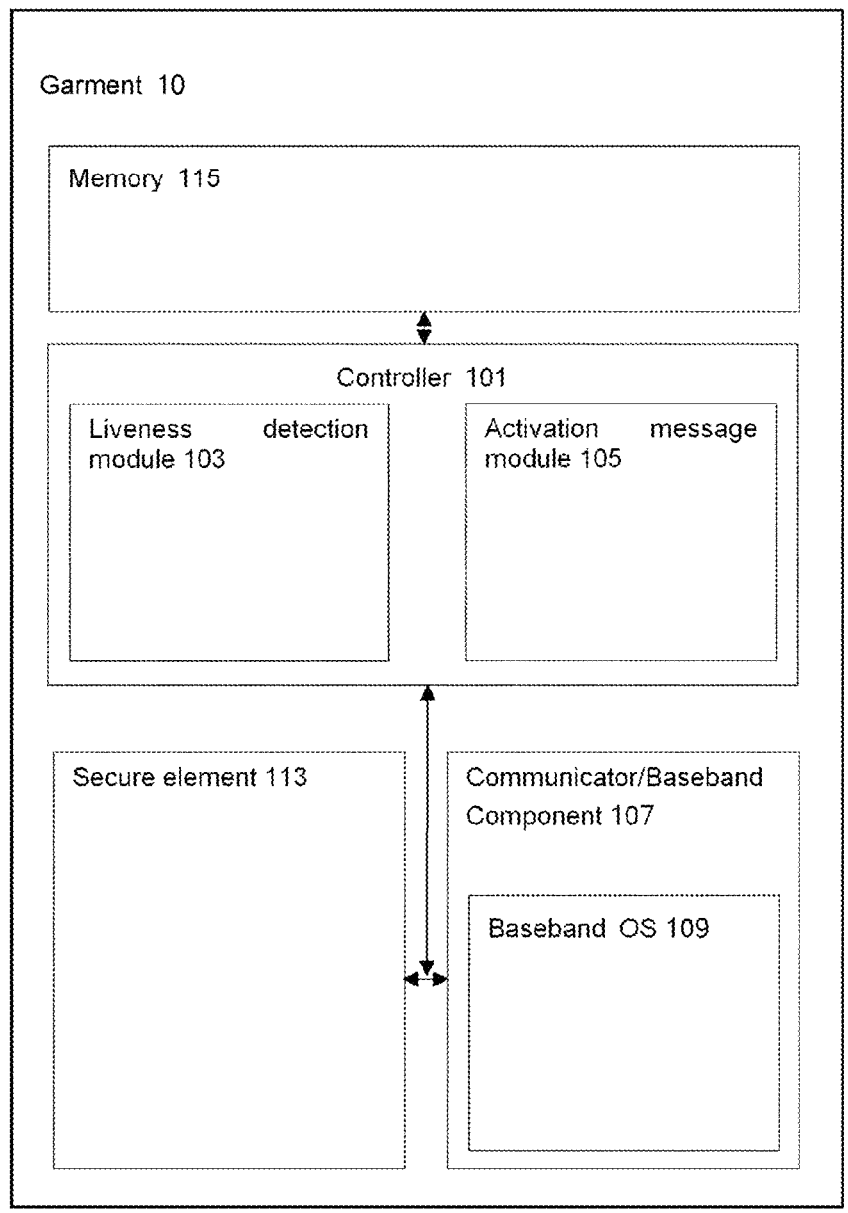
FIG. 1 shows a schematic diagram of an example garment according to aspects of the present disclosure.

Referring to FIG. 1, there is shown a garment 10 according to aspects of the present disclosure. The garment 10 comprises a controller 101. The controller 101 comprises a liveness detection module 103 and an activation message module 105. The garment 10 further comprises a communicator 107.

The liveness detection module 103 is arranged to detect whether the garment 10 is being worn by a user. The garment 10 further comprises at least one biosensing unit (not shown) which may be part of or may be separate to the liveness detection module 103. The biosensing unit is for measuring one or more biosignals of the wearer. In other words, the biosensing unit records biodata. The biodata is provided to the liveness detection module 103 which analyses the biodata to determine whether the garment 10 is being worn by a user. In some examples, the potential difference between electrodes of one or more biosensing units may be used to determine whether the garment is being worn. When the electrodes are placed in skin contact (or close to the skin) an electrical circuit may be completed between the electrodes via the skin, which may be detected and used to detect that the garment is being worn. Generally, many factors such as temperature, heart rate, breathing rate, or any other detected biosignal can be used to determine whether the garment 10 is being worn.

The activation message module 105 is arranged to generate an activation message for requesting that wireless network services be activated for the garment 10 in response to the liveness detection module 103 detecting that the garment is being worn. The activation message can be a request the activation (e.g. provisioning) of services originating from the garment 10. This may be referred to as a Mobile Originating Provisioning Request (MOPR) message. The activation message may be encrypted.

The communicator 107 is arranged to transmit the activation message to a server operable to activate wireless network services for the garment 10.

In an example, the communicator 107 transmits the activation message over a provisioning channel of the wireless network which may be a mobile network. The provisioning channel is available to inactive or unprovisioned wireless devices. Using the provisioning channel, the activation message can be delivered to the server for use in activating wireless network services for the garment 10. The provisioning channel may be, for example, an Unstructured Supplementary Service Data (USSD) channel, a Short Message Service (SMS) messaging channel or a Wireless Application Protocol (WAP) messaging channel, amongst others.

In another example, the communicator 107 transmits the activation message over a second wireless network that the garment 10 is already activated to communicate on. This means that before wireless network services for the garment 10 are activated, the garment 10 may use a different communication protocol to communicate the activation message to the server. The second wireless network may be a short-range local communication over WLAN, WLAN, WPAN, NFC, or Bluetooth for example. The garment 10 may communicate the activation message indirectly to the server via one or more wireless devices that the communicator 107 is operable to communicate with over the second wireless network. The communicator 107 may comprise a first communicator for communicating over the first wireless network which is desired to be activated and a second communicator for communicating over the second wireless network.

The communicator 107 in the example of FIG. 1 is in the form of a baseband component 107. The baseband component 107 includes a baseband OS 109 that is configured to manage hardware resources of the baseband component 107. The baseband component 107 may itself comprise a processor, a memory, and radio components to effect communication over a wireless network. The communicator 107 is not required to be a baseband component in all examples of the present example. Instead, the communicator 107 may be any form of communicator 107 operable to communicate data wirelessly via one or more base stations. The communicator 107 therefore provides wireless communication capabilities for the garment 10 and enables the garment 10 to communicate via one or more wireless communication protocols such as used for communication on: a wireless wide area network (WWAN), a wireless metroarea network (WMAN), a wireless local area network (WLAN), a wireless personal area network (WPAN), a near field communication (NFC), and a cellular communication network. The cellular communication network may be a fourth generation (4G) LTE, LTE Advanced (LTE-A), fifth generation (5G), sixth generation (6G), and/or any other present or future developed cellular wireless network.

The garment 10 also includes a secure element 113 and a memory 115. The secure element 113 may represent a removable UICC or an eUICC. The secure element 113 may store multiple different eSIMs for accessing different mobile network operators (MNOs). The garment may be subscribed to multiple different MNOs, and the secure element 113 may store an eSIM for each MNO to which the garment 10 is subscribed. The secure element 113 may store a subscriber identifier for the garment 10 which uniquely identifies the garment 10 on the mobile network. The subscriber identifier may comprise a mobile subscription identification number (MSIN). The subscriber identifier may comprise an international mobile subscriber identity (IMSI). The memory 115 may store a unique identifier for the garment 10. The unique identifier may be transmitted by the garment 10 to a server which may then use the unique identifier to determine the subscriber identifier. In this way, the subscriber identifier does not need to be transmitted to enable the wireless network services to be activated. The server may store a table linking different unique identifiers to different subscriber identifiers. The server may use the table to obtain the required subscriber identifier in response to receiving the unique identifier.

Figure 2:
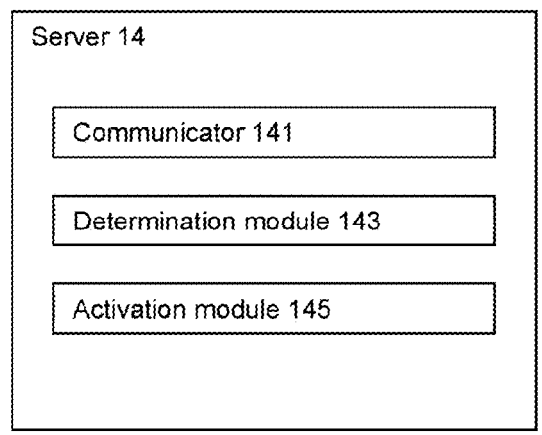
FIG. 2 shows a schematic diagram of an example server according to aspects of the present disclosure.

Referring to FIG. 2, there is shown a server 14 according to aspects of the present disclosure. The server 14 comprises a communicator 141, a determination module 143 and an activation module 145.

The communicator 141 is operable to receive the activation message from the garment 10 (FIG. 1). The determination module 143 is operable to determine whether to activate wireless network services for the garment 10. The activation module 145 is operable to activate wireless network services for the garment 10. In some examples, the determination module 143 determines to activate wireless network services for the garment 10 provided that an activation message is received. This may mean that only liveness detection is required to activate wireless network services for the garment 10.

As an example, garments may be provided to facilitate the monitoring of people during events such as music festivals which typically involve a large gathering of people. These garments are not initially activated to communicate over the wireless network to save wireless network subscriptions costs, for example. It would be desirable to monitor properties such as the movements, location, and biodata of the people so that festival organisers or health care professionals can monitor the festival goers and provide appropriate actions as required. For example, it may be desirable to monitor the movements of people at the festival for the purpose of crowd control or to help locate children who have strayed from their guardians. It may also be desirable to monitor the hydration levels and/or body temperature of the festival goers to reduce the risk of people becoming dehydrated and/or overheated. To this end, it is desirable to provide garments to monitor properties, such as the properties described above, of the festival goers. The garments may be distributed at the event and worn by the festival goers. The act of wearing the garment causes the garments to be activated to communicate over the wireless network. This approach provides an easy mechanism for activating garments on a wireless network and avoids the need for a complicated manual registration procedure.

In some examples, additional registration steps may be required by the user to, for example, purchase a data plan for the garment. These additional steps may need to be performed to enable the garment to freely transmit data over the wireless network. In other words, the activation of wireless network services performed in accordance with the present invention may only be an initial "out of the box" activation of the garment.

Figure 3:
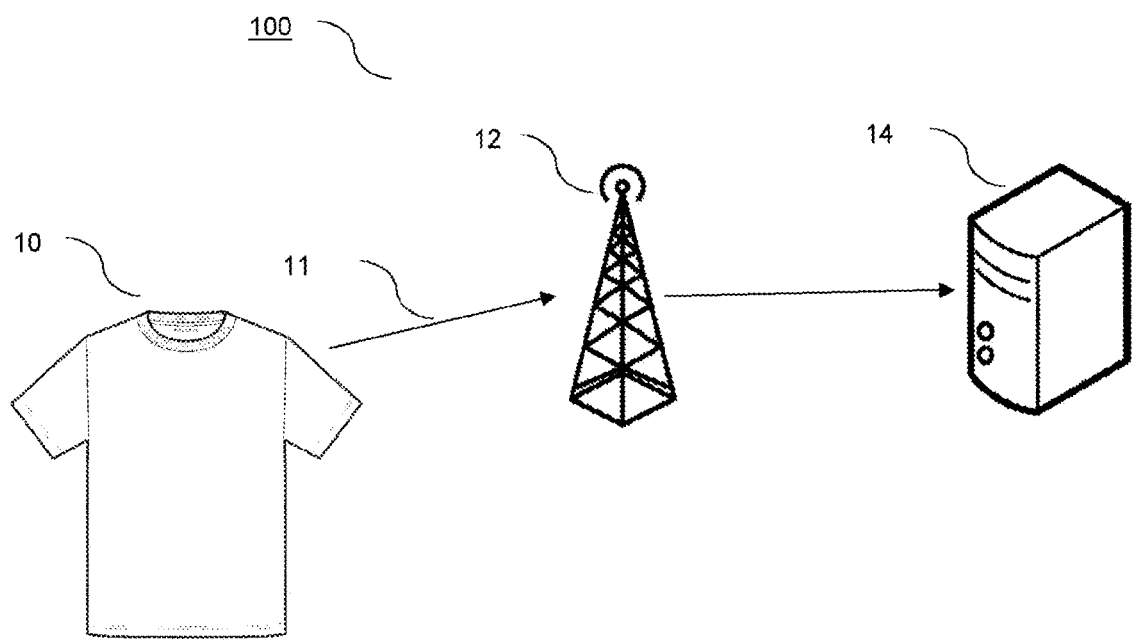
FIG. 3 shows a schematic diagram of an example system according to aspects of the present disclosure.

Referring to FIG. 3, there is shown a system 100 according to aspects of the present disclosure which is used to activate wireless network services for a garment 10. The garment 10 generates the activation message and transmits the activation message over a provisioning channel 11 provided on the wireless network represented by base station 12. The wireless network 12 that receives the activation message via the provisioning channel 11 provides the activation message to a server 14.

The server 14 is a mobile network operator server 14 run by the wireless network for the activation of services for wireless devices such as garment 10. The activation of services includes activating the garment 10 to communicate on the wireless network. This may be an initial "out of the box" activation of wireless services of an un provisioned garment. The activation of services includes device upgrades, device reactivations, wireless number changes, the addition or purchasing of services, and the wireless number porting for garments 10 that have already been activated/provisioned.

The server 14 may be a distributed network of servers. That is, aspects of the present disclosure may be performed by a distributed computing system that operate together to perform the desired function of the server 14.

Figure 4:
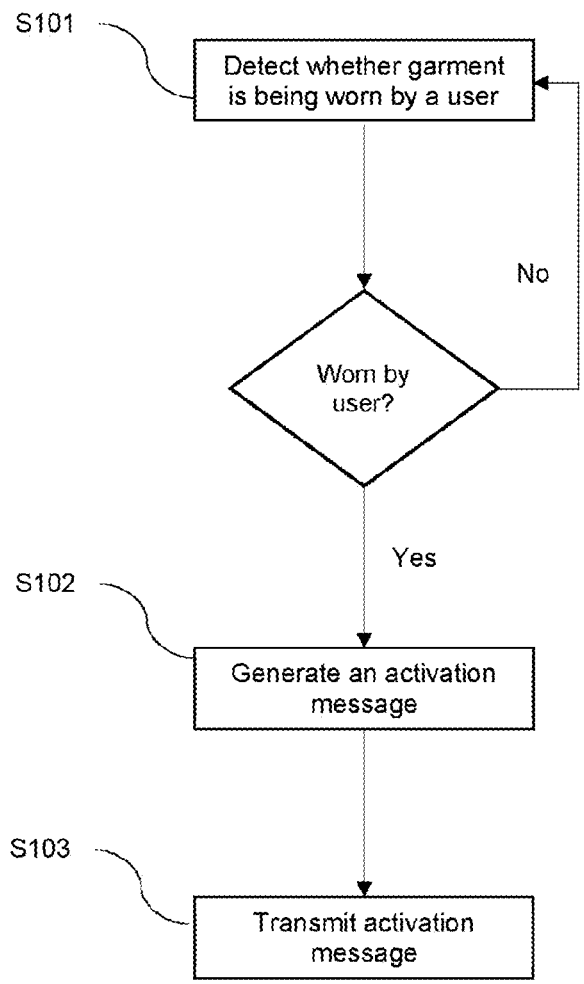
FIG. 4 shows a flow diagram of an example method according to aspects of the present disclosure.

Referring to FIG. 4, there is shown a flow diagram for an example method according to aspects of the present disclosure.

Step S101 of the method comprises detecting, by the garment, whether the garment is being worn by a user.

Step S102 of the method comprises, in response to detecting that the garment is being worn, generating, by the garment, an activation message for requesting that wireless network services be activated for the garment.

Step S103 of the method comprises transmitting, by the garment, the activation message to a server operable to activate wireless network services for the garment.

Figure 5:
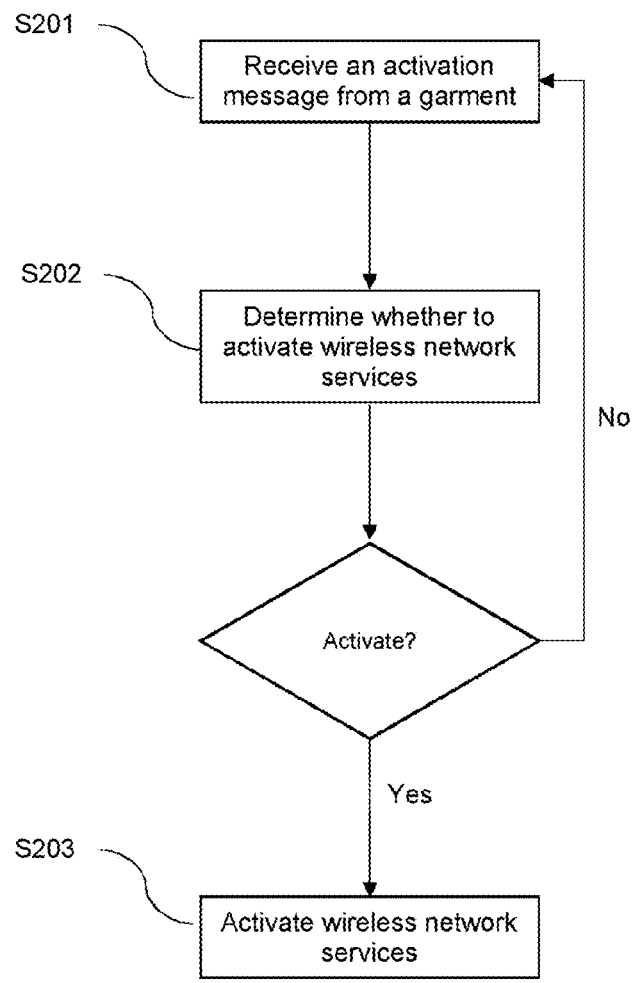
FIG. 5 shows a flow diagram of an example method according to aspects of the present disclosure.

Referring to FIG. 5, there is shown a flow diagram for an example method according to aspects of the present disclosure.

Step S201 of the method comprises receiving, by the server, an activation message from a garment, the activation message requesting that wireless network services be activated for the garment.

Step S202 of the method comprises determining, by the server, whether to activate wireless network services for the garment.

Step S203 of the method comprises activating wireless network services as a result of the determining performed in step S202.

At least some of the example embodiments described herein may be constructed, partially or wholly, using dedicated special-purpose hardware. Terms such as 'component', 'module' or 'unit' used herein may include, but are not limited to, a hardware device, such as circuitry in the form of discrete or integrated components, a Field Programmable Gate Array (FPGA) or Application Specific Integrated Circuit (ASIC), which performs certain tasks or provides the associated functionality. In some embodiments, the described elements may be configured to reside on a tangible, persistent, addressable storage medium and may be configured to execute on one or more processors. These functional elements may in some embodiments include, by way of example, components, such as software components, object-oriented software components, class components and task components, processes, functions, attributes, procedures, subroutines, segments of program code, drivers, firmware, microcode, circuitry, data, databases, data structures, tables, arrays, and variables. Although the example embodiments have been described with reference to the components, modules and units discussed herein, such functional elements may be combined into fewer elements or separated into additional elements. Various combinations of optional features have been described herein, and it will be appreciated that described features may be combined in any suitable combination. In particular, the features of any one example embodiment may be combined with features of any other embodiment, as appropriate, except where such combinations are mutually exclusive. Throughout this specification, the term "comprising" or "comprises" means including the component(s) specified but not to the exclusion of the presence of others.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

The invention claimed is:

1. A wearable device comprising:
   a liveness detection module arranged to detect whether the wearable device is being worn by a user;
   an activation message module arranged to generate an activation message for requesting that wireless network services over a first wireless network be activated for the wearable device in response to the liveness detection module detecting that the wearable device is being worn; and
   a communicator arranged to transmit the activation message indirectly to a server, via communication with a wireless device over a second wireless network that the wearable device is activated to transmit data on, the server being operable to, based on receiving the activation message, activate wireless network services over the first wireless network for the wearable device to enable the wearable device to directly transmit or receive data via over the first wireless network, wherein prior to the server receiving the activation message and activating the wireless network services, the wearable device is not able to directly transmit or receive data over the first wireless network,
   wherein the first wireless network is a cellular network, and the second wireless network is a short-range wireless network; and
   wherein the server comprises a determination module operable to activate the wireless network services over the first wireless network for the wearable device based on determining that status information for the wearable device indicates that the wearable device is authorized to be activated on the cellular network.

2. The wearable device as claimed in claim 1, wherein the activation message comprises identification information for the wearable device.

3. The wearable device as claimed in claim 2, wherein the identification information for the wearable device comprises a unique identifier for the wearable device and/or a subscriber identifier for the wearable device which uniquely identifies the wearable device on the cellular network.

4. The wearable device as claimed in claim 3, wherein the identification information comprises the subscriber identifier, and the subscriber identifier comprises a mobile subscription identification number (MSIN).

5. The wearable device as claimed in claim 4, wherein the identification information comprises the subscriber identifier, and the subscriber identifier comprises an international mobile subscriber identity (IMSI).

6. The wearable device as claimed in claim 1, wherein the wearable device further comprises a secure element that represents an embedded Universal Integrated Circuit Card (eUICC).

7. The wearable device as claimed in claim 1, wherein prior to the liveness detection module detecting that the wearable device is being worn by a user, the wearable device is arranged to operate in a low power mode.

8. The wearable device as claimed in claim 7, wherein if the liveness detection module detects that the wearable device is being worn by a user, the wearable device is arranged to transition from the low power mode to a normal mode.

9. The wearable device as claimed in claim 7, wherein in the low power mode the communicator is not activated to transmit data.

10. The wearable device as claimed in claim 8, wherein in the normal mode, the communicator is activated to transmit data.

11. The wearable device as claimed in claim 1, wherein the wearable device is a garment.

12. The wearable device as claimed in claim 1, wherein the wearable device comprises a biosensing unit for measuring biosignals of the user.

13. The wearable device as claimed in claim 1, wherein determining that status information for the wearable device indicates that the wearable device is authorized to be activated on the cellular network comprises determining that the wearable device is associated with a cellular data plan.

14. The wearable device as claimed in claim 1, wherein the server is operable to, based on receiving activation messages from a plurality of wearable device associated with a current event, activate wireless network services over the first wireless network for the plurality of wearable devices.

15. A method of requesting wireless network services for a wearable device, the method comprising:
    detecting, by the wearable device, whether the wearable device is being worn by a user;
    in response to detecting that the wearable device is being worn, generating, by the wearable device, an activation message for requesting that wireless network services over a first wireless network be activated for the wearable device; and
    transmitting, by the wearable device, the activation message indirectly to a server, via communication with a wireless device over a second wireless network that the wearable device is activated to transmit data on, the server being operable to, based on receiving the activation message, activate wireless network services over the first wireless network for the wearable device to enable the wearable device to directly transmit or receive data via over the first wireless network, wherein prior to the server receiving the activation message and activating the wireless network services, the wearable device is not able to directly transmit or receive data over the first wireless network,
    wherein the first wireless network is a cellular network, and the second wireless network is a short-range wireless network; and
    wherein the server comprises a determination module operable to activate the wireless network services over the first wireless network for the wearable device based on determining that status information for the wearable device indicates that the wearable device is authorized to be activated on the cellular network.

16. The method of claim 15, wherein determining that status information for the wearable device indicates that the wearable device is authorized to be activated on the cellular network comprises determining that the wearable device is associated with a cellular data plan.

17. The method of claim 15, wherein the server is operable to, based on receiving activation messages from a plurality of wearable device associated with a current event, activate wireless network services over the first wireless network for the plurality of wearable devices.

18. The method of claim 15, wherein the activation message comprises identification information for the wearable device.

19. The method of claim 18, wherein the identification information for the wearable device comprises a unique identifier for the wearable device and/or a subscriber identifier for the wearable device which uniquely identifies the wearable device on the cellular network.

20. The method of claim 19, wherein the identification information comprises the subscriber identifier, and the subscriber identifier comprises a mobile subscription identification number (MSIN) or an international mobile subscriber identity (IMSI).

* * * * *